US009307958B2

(12) United States Patent
Nishihara et al.

(10) Patent No.: US 9,307,958 B2
(45) Date of Patent: Apr. 12, 2016

(54) ULTRASONIC DIAGNOSTIC APPARATUS AND AN ULTRASONIC IMAGE PROCESSING APPARATUS

(75) Inventors: Kuramitsu Nishihara, Otawara (JP); Tomohisa Imamura, Nasushiobara (JP); Atsushi Sumi, Otawara (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 198 days.

(21) Appl. No.: 13/197,176

(22) Filed: Aug. 3, 2011

(65) Prior Publication Data

US 2012/0035478 A1    Feb. 9, 2012

(30) Foreign Application Priority Data

Aug. 5, 2010    (JP) .................................. 2010-176733

(51) Int. Cl.
| | |
|---|---|
| *A61B 8/00* | (2006.01) |
| *A61B 8/08* | (2006.01) |
| *G01S 7/52* | (2006.01) |
| *G06T 5/00* | (2006.01) |
| *G01S 15/89* | (2006.01) |

(52) U.S. Cl.
CPC ........... *A61B 8/5269* (2013.01); *G01S 7/52074* (2013.01); *G01S 7/52077* (2013.01); *G01S 15/8993* (2013.01); *G06T 5/003* (2013.01); *A61B 8/0866* (2013.01); *A61B 8/466* (2013.01); *A61B 8/483* (2013.01); *G01S 15/8979* (2013.01); *G06T 2207/10136* (2013.01); *G06T 2207/20016* (2013.01); *G06T 2207/20064* (2013.01); *G06T2207/20192* (2013.01); *G06T 2207/30044* (2013.01)

(58) Field of Classification Search
CPC .... A61B 8/5269; A61B 8/0866; A61B 8/466; A61B 8/483; G01S 7/52074; G01S 7/52077; G01S 15/8993; G01S 15/8979; G06T 5/003; G06T 2207/10136; G06T 2207/20016; G06T 2207/20064; G06T 2207/20192; G06T 2207/30044
See application file for complete search history.

(56) References Cited

U.S. PATENT DOCUMENTS 5,000,183 A    3/1991    Bonnefous
2009/0171208 A1    7/2009    Osumi et al.

FOREIGN PATENT DOCUMENTS

| | | |
|---|---|---|
| EP | 1647935 A2 | 4/2006 |
| JP | 2005296331 A | 10/2005 |
| JP | 2009-153918 A | 7/2009 |

OTHER PUBLICATIONS

Chinese Office Action with English Translation for Chinese Patent Application No. 201110223571.8 mailed on May 2, 2013.

*Primary Examiner* — Bo J Peng
(74) *Attorney, Agent, or Firm* — Yoshida & Associates, LLC (57) ABSTRACT

According to one embodiment, an ultrasonic diagnostic apparatus comprises a decomposition unit, a filtering unit, a level control unit and a mixing unit. The decomposition unit hierarchically performs multi-resolution decomposition of the ultrasonic image data and acquires low-frequency decomposed image data with first to n-th levels and high-frequency decomposed image data with first to n-th levels. The filtering unit calculates a filter coefficient using the high-frequency decomposed image data and uses the filter coefficient to perform nonlinear anisotropic diffusion filtering on the low-frequency decomposed image data or output data and generate edge information on a signal. The control unit controls a signal level of the high-frequency decomposed image data. The mixing unit acquires ultrasonic image data by hierarchically performing multi-resolution mixing of output data of the filtering unit or output data from a next lower layer and output data of the high-frequency level control unit.

12 Claims, 11 Drawing Sheets

ULTRASONIC DIAGNOSTIC APPARATUS AND AN ULTRASONIC IMAGE PROCESSING APPARATUS

CROSS-REFERENCE TO RELATED APPLICATIONS

This application is based upon and claims the benefit of priority from prior Japanese Patent Application No. 2010-176733, filed Aug. 5, 2010, the entire contents of which are incorporated herein by reference.

FIELD

Embodiments described herein relate generally to an ultrasonic diagnostic apparatus and an ultrasonic image processing apparatus.

BACKGROUND

Ultrasonic diagnosis makes it possible to display the pulsation of the heart or the movement of an embryo in real time by a simple operation of bringing an ultrasonic probe into contact with a body surface. In addition, since the ultrasonic diagnosis is highly safe, the test may be repeatedly performed. In addition, the system size is small compared with other diagnostic apparatuses, such as an X ray, a CT, and an MRI, and a test at the bedside can also be easily performed. For this reason, it can be said that the ultrasonic diagnosis is an easy diagnostic method. An ultrasonic diagnostic apparatus used in the ultrasonic diagnosis varies in various ways with the type of a function that the ultrasonic diagnostic apparatus has. As a small ultrasonic diagnostic apparatus, an ultrasonic diagnostic apparatus that is so small that it can be carried with one hand has been developed. In addition, since the ultrasonic diagnosis does not cause radioactive exposure unlike the X ray, the ultrasonic diagnosis may also be used in an obstetric treatment, a remote medical treatment, and the like. In addition, a recent ultrasonic diagnostic apparatus may collect three-dimensional biological information (volume data) by spatially scanning the inside of the tested body using an ultrasonic probe with a two-dimensional array in which ultrasonic vibrators are arrayed in a two-dimensional manner.

A conventional technique for the purpose of speckle reduction in the ultrasonic diagnosis includes filtering processing including a combination of multi-resolution analysis and a nonlinear anisotropic diffusion filter. In the nonlinear anisotropic diffusion processing, different processings are applied to edge portions and the other portions, so that an image with edge emphasis and speckle reduction can be obtained. In the multi-resolution analysis, processings proceed from macro-scale processing to more local processing in order, and this enables fast and efficient processing.

However, when the state of an embryo is observed particularly in a three-dimensional manner with the above conventional filtering technique, relatively large recesses and protrusions on the surface of the face of the embryo are detected as edges in a lower level processing of the multi-resolution analysis. Accordingly, since the edges of recesses and protrusions are emphasized as described above, they may be incorrectly recognized as edges in an upper level processing of the multi-resolution analysis. As a result, the edges may be unnaturally emphasized in an output image. On the other hand, small edges that can be detected only in the upper level, such as fingers, are affected by lower speckle reduction, and therefore, it may be difficult to detect them as edges in the output image.

DETAILED DESCRIPTION

In general, according to one embodiment, an ultrasonic diagnostic apparatus includes a data generating unit, a decomposition unit, a filtering unit, a high-frequency level control unit and a mixing unit. The data generating unit is configured to execute transmission and reception of an ultrasonic wave in a B-mode with respect to a predetermined region of a tested body and generates ultrasonic image data. The decomposition unit is configured to hierarchically perform multi-resolution decomposition of the ultrasonic image data and acquire low-frequency decomposed image data with first to n-th levels (where, "n" is a natural number equal to or larger than 2) and high-frequency decomposed image data with first to n-th levels. The filtering unit is configured to calculate a filter coefficient using the high-frequency decomposed image data in each layer and use the filter coefficient to perform nonlinear anisotropic diffusion filtering on the low-frequency decomposed image data or output data from a next lower layer and generate edge information on a signal, for every layer, from the high-frequency decomposed image data. The high-frequency level control unit is configured to control a signal level of the high-frequency decomposed image data for every layer on the basis of the edge information of each of the layers. The mixing unit is configured to acquire ultrasonic image data by hierarchically performing multi-resolution mixing of output data of the filtering unit or output data from a next lower layer and output data of the high-frequency level control unit.

Hereinafter, the first to fourth embodiments will be described with reference to the drawings. In the following description, constituent elements having approximately the same function and configuration are denoted with the same reference numeral, and repeated explanation thereabout will be made only when it is necessary.

First Embodiment

Hereinafter, the first embodiment will be explained with reference to the drawings. In the following description, constituent elements having approximately the same function and configuration are denoted with the same reference numeral, and repeated explanation thereabout will be made only when it is necessary.

Figure 1:
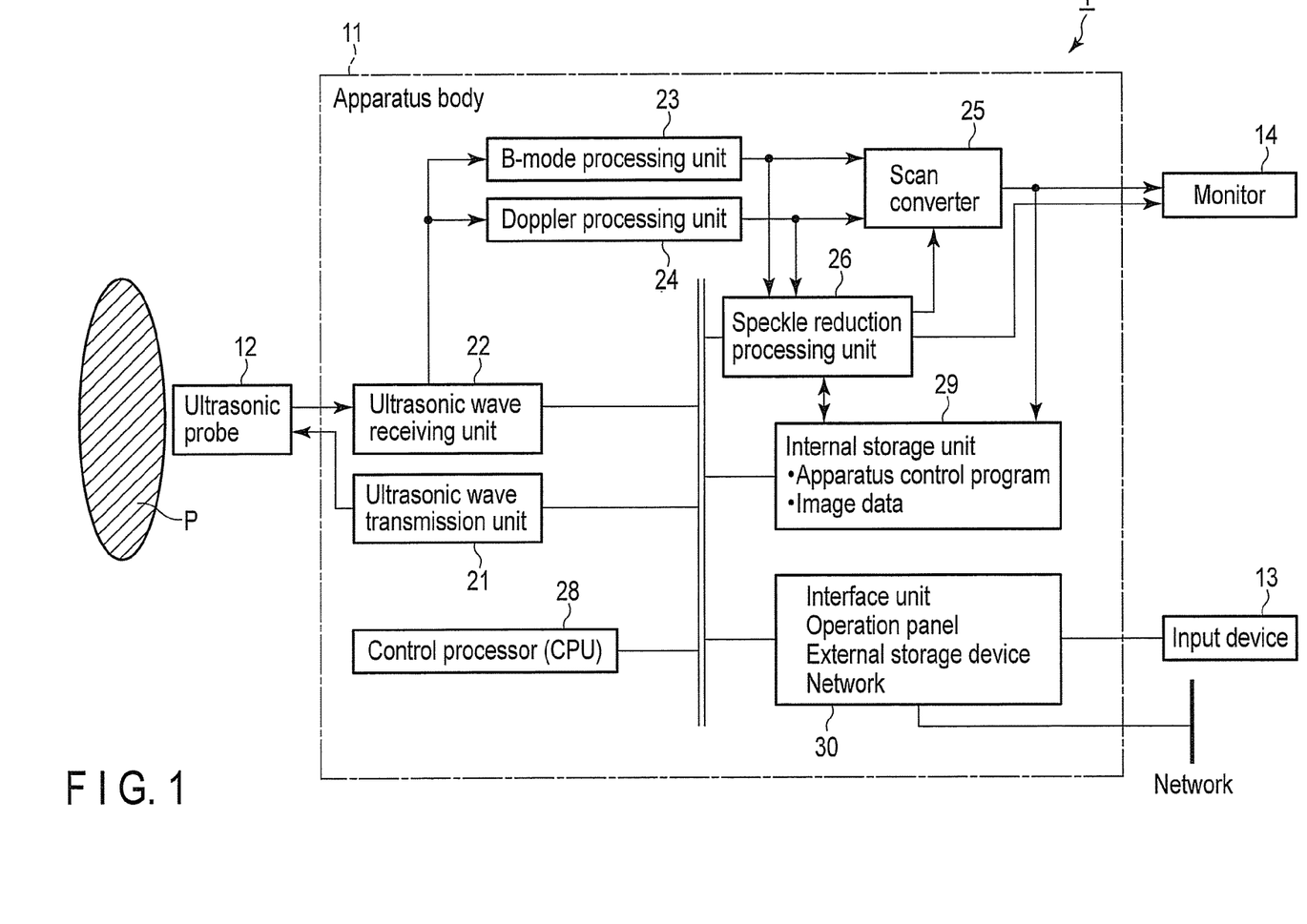
FIG. 1 is a block configuration diagram illustrating a configuration of an ultrasonic diagnostic apparatus 1 according to an embodiment.

FIG. 1 is a block configuration diagram illustrating a configuration of an ultrasonic diagnostic apparatus 1 according to the present embodiment. As shown in the drawing, the ultrasonic diagnostic apparatus 1 includes an ultrasonic probe 12, an input device 13, a monitor 14, an ultrasonic wave transmission unit 21, an ultrasonic wave receiving unit 22, a B-mode processing unit 23, a Doppler processing unit 24, a scan converter 25, a speckle reduction processing unit 26, a control processor (CPU) 28, an internal storage unit 29, and an interface unit 30. Hereinafter, the function of each constituent element will be explained.

The ultrasonic probe 12 generates an ultrasonic wave on the basis of a driving signal from the ultrasonic wave transmission unit 21 and has a plurality of piezoelectric vibrators that convert a reflected wave from a tested body into an electric signal, a matching layer provided in the piezoelectric vibrators, a packing material that prevents propagation of an ultrasonic wave rearward from the piezoelectric vibrators, and the like. When ultrasonic waves are transmitted from the ultrasonic probe 12 to a tested body P, the transmitted ultrasonic waves are sequentially reflected on a discontinuous surface of acoustic impedances of body tissues and are then received as an echo signal by the ultrasonic probe 12. The amplitude of the echo signal depends on a difference of acoustic impedances on the discontinuous surfaces on which the ultrasonic waves are reflected. In addition, when transmitted ultrasonic pulses are reflected by a surface of a moving blood flow, a heart wall, and the like, an echo is affected by frequency deviation depending on a speed component of a moving body in the ultrasonic wave transmission direction due to the Doppler effect.

The input device 13 is connected to an apparatus body 11 and has various switches, buttons, a track ball 13s, a mouse 13c, a keyboard 13d, and the like, which are used to receive, from an operator, various kinds of instructions, an instruction for setting a condition or a region of interest (ROI), an instruction for setting various image quality conditions, and the like, and take them into the apparatus body 11. For example, when a user operates a stop button or a FREEZE button of the input device 13, transmission and reception of an ultrasonic wave are stopped and the ultrasonic diagnostic apparatus is temporarily kept in a halted state.

The monitor 14 displays, as an image, morphological information or blood flow information in a living body on the basis of a video signal from the scan converter 25.

The ultrasonic wave transmission unit 21 has a trigger generating circuit, a delay circuit, and a pulse circuit which are not shown. The pulse circuit repeatedly generates a rate pulse for forming a transmitted ultrasonic wave at a predetermined rate frequency fr Hz (with a cycle of 1/fr second). The delay circuit makes ultrasonic waves converge in the beam shape for every channel and gives a delay time, which is required for determining transmission directivity, to each rate pulse. The trigger generating circuit applies a driving pulse to the probe 12 with timing based on the rate pulse.

The ultrasonic wave transmission unit 21 has a function of instantly changing a transmission frequency, a transmitted driving voltage, and the like in order to execute a predetermined scan sequence according to the instruction of the control processor 28. In particular, the change of the transmitted driving voltage is realized by a linear amplifier type signal transmission circuit capable of changing the value instantaneously or a mechanism for electrically switching a plurality of power supply units.

The ultrasonic wave receiving unit 22 has an amplifying circuit, an A/D converter, an adder, and the like which are not shown. The amplifying circuit amplifies an echo signal received through the probe 12 for every channel. The A/D converter gives a delay time, which is required to determine the receiving directivity, to the amplified echo signal, and then the adder performs adding processing. As a result of this addition, a reflected component in a direction according to the receiving directivity of echo signals is emphasized, and overall beam of ultrasonic transmission and reception is formed by the receiving directivity and the transmission directivity.

The B-mode processing unit 23 receives an echo signal from the ultrasonic wave receiving unit 22, performs logarithmic amplification and envelope detection processing, and generates data in which the signal strength is expressed as brightness. The data are transmitted to the scan converter 25 and is displayed on the monitor 14 as a B-mode image in which the strength of a reflected wave is expressed as the brightness.

The Doppler processing unit 24 makes a frequency analysis of speed information from the echo signal received from the ultrasonic wave receiving unit 22, extracts a blood flow or a tissue and a contrast echo component due to the Doppler effect, and calculates blood flow information, such as an average speed, diffusion, and power, with respect to multiple points. The acquired blood flow information is transmitted to the scan converter 25 to be color-displayed on the monitor 14 as an average speed image, a diffusion image, a power image, and a combination image thereof.

The scan converter 25 mixes a scanning line signal row of ultrasonic scan with character information, scale, and the like of various parameters of data received from the B-mode processing unit 23, the Doppler processing unit 24, and the speckle reduction processing unit 26, converts the result into a scanning line signal row in a typical video format represented by a television, and generates an ultrasonic diagnostic image as a display image. The scan converter 25 has a storage memory in which image data is stored, for example, so that after diagnosis, an operator can load an image recorded during a test. It should be noted that data that have not yet input to the scan converter 25 are a set of amplitude values or brightness values for every spatial position and are called "raw data".

The speckle reduction processing unit 26 executes processing according to a speckle reduction function, which will be described later, on the basis of the control of the control processor 28 using the raw data prior to scan conversion.

The control processor 28 has a function as an information processing device (computer), and is a control unit that controls an operation of the ultrasonic diagnostic apparatus body.

The control processor 28 reads from the internal storage unit 29 a control program for executing a dedicated program for executing image generation/display and speckle reduction function, explained later, loads the program onto the memory of the control processor 28, and executes calculation, control, and the like on various kinds of processing.

The internal storage unit 29 stores a control program for executing scan sequence, image generation, and display processing, explained later, diagnostic information (for example, a patient ID and doctor's opinion), a diagnostic protocol, transmission and reception conditions, and a dedicated program for realizing the speckle reduction function, a body mark generating program, and other data groups. In addition, the internal storage unit 29 may also be used to store an image in the image memory 26 as necessary. The data in the internal storage unit 29 may also be transmitted to an external peripheral device through the interface circuit 30.

The interface unit 30 is an interface related to the input device 13, a network, and a new external storage device (not shown). Data or an analysis result of an ultrasonic image obtained by the apparatus may be transmitted to other apparatuses through the network by the interface unit 30.

(Speckle Reduction Function)

Next, a speckle reduction function that the ultrasonic diagnostic apparatus 1 has will be described. In this function, nonlinear anisotropic diffusion filter processing for achieving edge emphasis and speckle reduction is executed, on image data (raw data) prior to scan conversion processing, in combination with multi-resolution analysis in which processings proceed from macro-scale processing to more local processing in order. At this occasion, high-frequency decomposed image data obtained from multi-resolution analysis are used as an input to edge detection algorithm, and in the diffusion processing executed after the edge detection, the edge information detected by the high-frequency decomposed image data and the low-frequency decomposed image data are used to perform speckle reduction with the synergistic effect of the multi-resolution decomposition and the nonlinear anisotropic diffusion filter processing. In the present embodiment, for example, the number n of levels of multi-resolution decomposition is assumed to be 3 for the sake of concrete explanation. However, the number n is not limited to the above example, and may be any value as long as the number n is a natural number equal to or larger than 2, for example.

Figure 2:
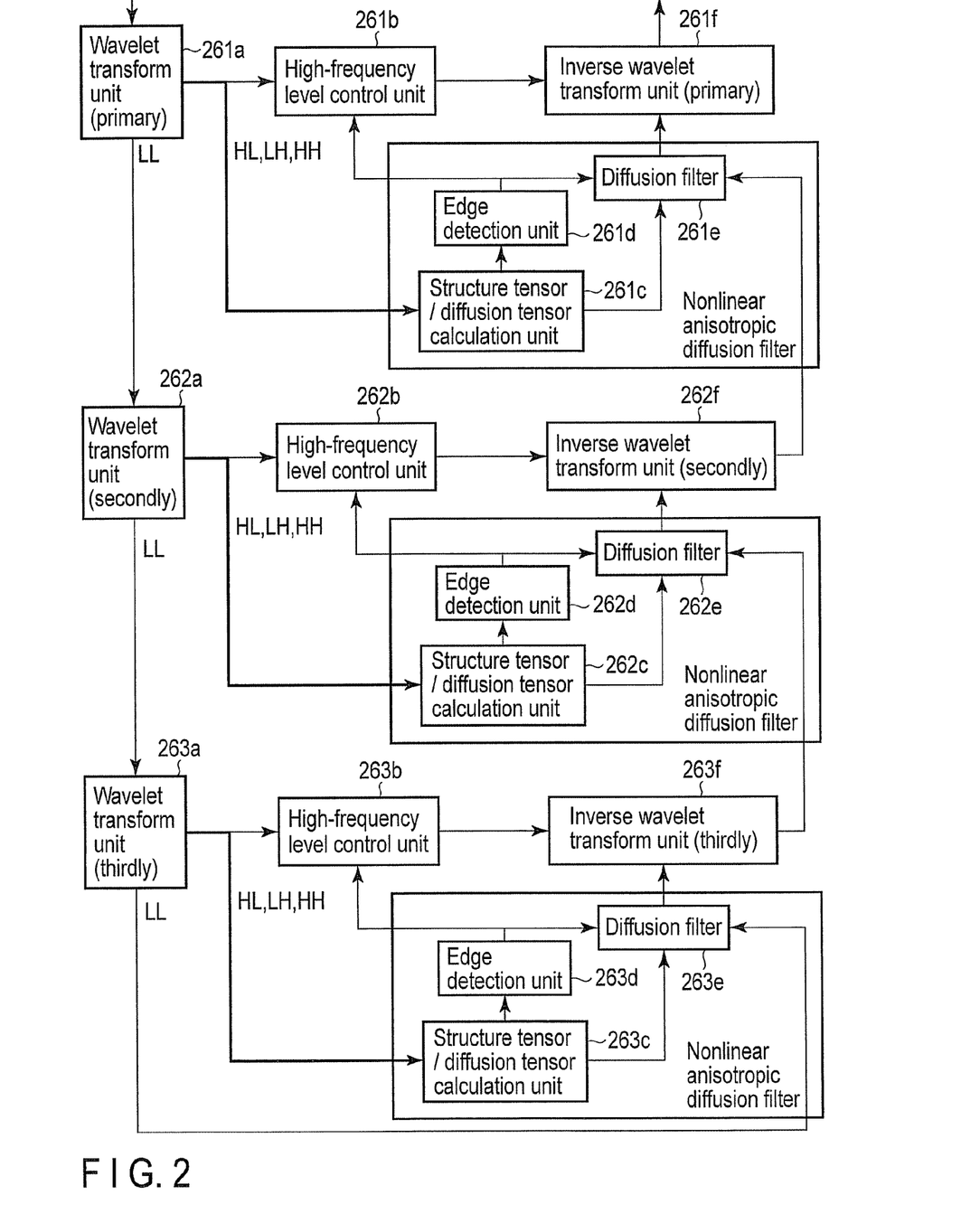
FIG. 2 is a diagram illustrating a flow of speckle reduction processing executed by a speckle reduction processing unit 26 according to the present embodiment.

FIG. 2 is a diagram illustrating a flow of processing according to the speckle reduction function executed by the speckle reduction processing unit 26 (speckle reduction processing). As shown in the drawing, first, a wavelet transform portion 261a of level 1 performs multi-resolution decomposition of image data (raw data) input from the B-mode processing unit 23. In this case, the "wavelet transform" means discrete wavelet transform. It should be noted that the wavelet transform is only an example of multi-resolution decomposition, and the multi-resolution decomposition is not limited to the above method. For example, the multi-resolution decomposition may also be realized by other methods, such as the Laplacian pyramid method. As a result of the multi-resolution decomposition, image data after decomposition is decomposed into a low-frequency image (LL), a horizontal direction high-frequency image (LH), a vertical direction high-frequency image (HL), and a diagonal direction high-frequency image (HH), of which horizontal and vertical lengths are half of those before the decomposition. Among the decomposed image data, the low-frequency image (LL) is output to a wavelet transform unit 262a of level 2, and the horizontal direction high-frequency image (LH), the vertical direction high-frequency image (HL), and the diagonal direction high-frequency image (HH) are respectively output to a high-frequency level control portion 261b and a structure tensor/diffusion tensor calculation unit 261c of level 1.

The wavelet transform unit 262a of level 2 acquires the low-frequency image (LL), the horizontal direction high-frequency image (LH), the vertical direction high-frequency image (HL), and the diagonal direction high-frequency image (HH) by performing multi-resolution decomposition of the low-frequency image (LL) input from the wavelet transform unit 261a of level 2. Then, the wavelet transform unit 262a outputs the low-frequency image (LL) to the wavelet transform unit 263a of level 3 and outputs the horizontal direction high-frequency image (LH), the vertical direction high-frequency image (HL), and the diagonal direction high-frequency image (HH) to the high-frequency level control unit 262b and the structure tensor/diffusion tensor calculation unit 262c of level 2.

The wavelet transform unit 263a of level 3 acquires the low-frequency image (LL), the horizontal direction high-frequency image (LH), the vertical direction high-frequency image (HL), and the diagonal direction high-frequency image (HH) by performing multi-resolution decomposition of the low-frequency image (LL) input from the wavelet transform unit 262a of level 2. The wavelet transform unit 263a outputs the low-frequency image (LL) to a nonlinear anisotropic diffusion filter 263e of level 3 and outputs the horizontal direction high-frequency image (LH), the vertical direction high-frequency image (HL), and the diagonal direction high-frequency image (HH) to a high-frequency level control unit 263b and a structure tensor/diffusion tensor calculation unit 263c of level 3.

The wavelet transform unit 263a of level 3 preferably outputs one image obtained by combining the horizontal direction high-frequency image (LH), the vertical direction high-frequency image (HL), and the diagonal direction high-frequency image (HH) to the structure tensor/diffusion tensor calculation unit 263c in order to increase the speed of the processing. Specific examples of images obtained by methods for combining images into one image include an image obtained by calculating absolute values of the three images and adding the absolute values, an image obtained by adding the three images (without calculating the absolute values), an average value image of the three images, an image obtained by adding the three images by predetermined weighting, and an image obtained by calculating absolute values of only several images of the three images and adding them (for example, an image obtained by the absolute values for only the diagonal direction high-frequency image (HH) without calculating the absolute values for the horizontal direction high-frequency image (LH) and the vertical direction high-frequency image (HL) and adding them).

Subsequently, a tensor/diffusion tensor calculation unit 263c of level 3 calculates a structure tensor and a diffusion tensor using the horizontal direction high-frequency image (LH), the vertical direction high-frequency image (HL), and the diagonal direction high-frequency image (HH). More specifically, the following processing is executed. The nonlinear anisotropic diffusion filter is expressed by the following partial differential equation (1).

$$\frac{\partial I}{\partial t} = div[D \nabla I] \quad (1)$$

"I" indicates a pixel level of an image to be processed, "∇I" indicates the gradient vector, and "t" indicates a time taken for processing. "D" indicates diffusion tensor and may be expressed by the following expression (2).

$$D = \begin{pmatrix} d_{11} & d_{12} \\ d_{12} & d_{22} \end{pmatrix} = R \begin{pmatrix} \lambda_1 & 0 \\ 0 & \lambda_2 \end{pmatrix} R^T \quad (2)$$

"R" indicates a rotation matrix, and the diffusion tensor D indicates an operation of applying coefficients $\lambda_1$ and $\lambda_2$ to the gradient vector of each pixel in a specific direction and a direction perpendicular to the specific direction. The direction is a direction of the edge of a detected image, and the coefficient depends on the size of the edge.

In order to detect the size and direction of the edge, structure tensor of the image is calculated, and an eigenvalue and an eigenvector are calculated in general. The eigenvalue is related with the size of the edge, and the eigenvector indicates the direction of the edge. The structure tensor is defined as the following expression (3).

$$S = G_\rho * \begin{pmatrix} I_x^2 & I_x I_y \\ I_x I_y & I_y^2 \end{pmatrix} = \begin{pmatrix} G_\rho * I_x^2 & G_\rho * (I_x I_y) \\ G_\rho * (I_x I_y) & G_\rho * I_y^2 \end{pmatrix} = \begin{pmatrix} s_{11} & s_{12} \\ s_{12} & s_{22} \end{pmatrix} \quad (3)$$

In this case, "$I_x$" and "$I_y$" indicate spatial differentiation of the image I to be processed in x (horizontal) and y (vertical) directions thereof, "Gp" indicates a two-dimensional Gaussian function, and an operator "*" indicates convolution. Calculation of the size and direction of an edge may not be necessarily performed strictly according to the above method. Instead of calculating $I_x$ and $I_y$ as a first step of processing, a sobel filter or a high-frequency component of multi-resolution decomposition may also be applied.

Although a method of calculating the coefficients $\lambda_1$ and $\lambda_2$ changes according to characteristics of an ultrasonic image in each diagnostic field, it is useful to prepare a general expression so that the coefficients can be adjusted by some parameters.

On the other hand, the calculation of the filter itself is performed according to a numeric analysis method of a partial differential equation. That is, from a pixel level of a pixel at a predetermined point and pixel levels of, for example, nine pixels around the pixel and each element value of diffusion tensor at time t, a new pixel level at the point is calculated at time t+Δt. Then, the same calculation is repeated once to several times adopting t+Δt as a new t.

Subsequently, an edge detection unit 263d calculates the sizes of edges (edge information) from each element of the structure tensor calculated by the structure tensor/diffusion tensor calculation unit 263c. The calculated edge information is output to the diffusion filter 263e. The high-frequency level control unit 263b of level 3 receives the horizontal direction high-frequency image (LH), the vertical direction high-frequency image (HL), the diagonal direction high-frequency image (HH), and edge information on these three components, and controls a high-frequency level according to the images and the edge information. In the present embodiment, the edge information is the size of an edge standardized on the basis of the eigenvalue of the structure tensor, a product of the size and each high-frequency image is taken for every pixel, and a control coefficient of each high-frequency image is applied to the result. As another example, there is a method of setting a threshold value for the size of an edge, determining the size of an edge equal to or larger than the threshold value as an edge, and applying a control coefficient of each high-frequency image to a region other than the edge. In this manner, the three high-frequency images processed as described above are input to a diffusion filter 263e and an inverse wavelet transform unit 263f.

Subsequently, the diffusion filter 263e of level 3 filters the three high-frequency images received from the high-frequency level control unit 263b, the edge information received from the edge detection unit 263d, and the low-frequency image (LL) received from the wavelet transform unit 263a, and outputs the low-frequency image, on which the edge emphasis and the speckle reduction in level 3 are executed, to the inverse wavelet transform unit 263f.

The high-frequency level control unit 263b uses the horizontal direction high-frequency image (LH), the vertical direction high-frequency image (HL), and the diagonal direction high-frequency image (HH) received from the wavelet transform unit 263a and uses the edge information received from the edge detection unit 263d to control the signal level of the high-frequency decomposed image data, and thereafter outputs the high-frequency decomposed image data to the inverse wavelet transform unit 263f.

The inverse wavelet transform unit 263f restructures one image using the high-frequency image and low-frequency image data received from the diffusion filter 263e and the high-frequency image data received from the high-frequency level control unit 263b. The horizontal and vertical lengths of the restructured image are twice those of an input image.

The restructured image output from the inverse wavelet transform unit 263f of level 3 is output to the diffusion filter 262e of level 2. In level 2, substantially the same processing as that of level 3 is executed using the restructured image output from level 3 and the horizontal direction high-frequency image (LH), the vertical direction high-frequency image (HL), and the diagonal direction high-frequency image (HH) output from the wavelet transform unit 262a. The restructured image output from the inverse wavelet transform unit 262f of level 2 is output to the diffusion filter 261e of level 1. In level 1, substantially the same processing as those of levels 2, 3 is executed using the restructured image output from level 2 and the horizontal direction high-frequency image (LH), the vertical direction high-frequency image (HL), and the diagonal direction high-frequency image (HH) output from the wavelet transform unit 261a. As a result of these processings, image data having been efficiently subjected to the edge emphasis and the speckle reduction are ultimately generated in the inverse wavelet transform unit 261f, and the image data are output to the scan converter 25.

The scan converter 25 mixes the composite image data with character information, scale, and the like of various parameters, converts the result into a scanning line signal sequence in a generally-available video format such as a television, and generates an ultrasonic diagnostic image as a display image. The generated ultrasonic image is displayed on the monitor 14 in a predetermined form.

Subsequently, the effects of the ultrasonic diagnostic apparatus according to the present embodiment will be explained while it is compared with a conventional technique.

Figure 3:
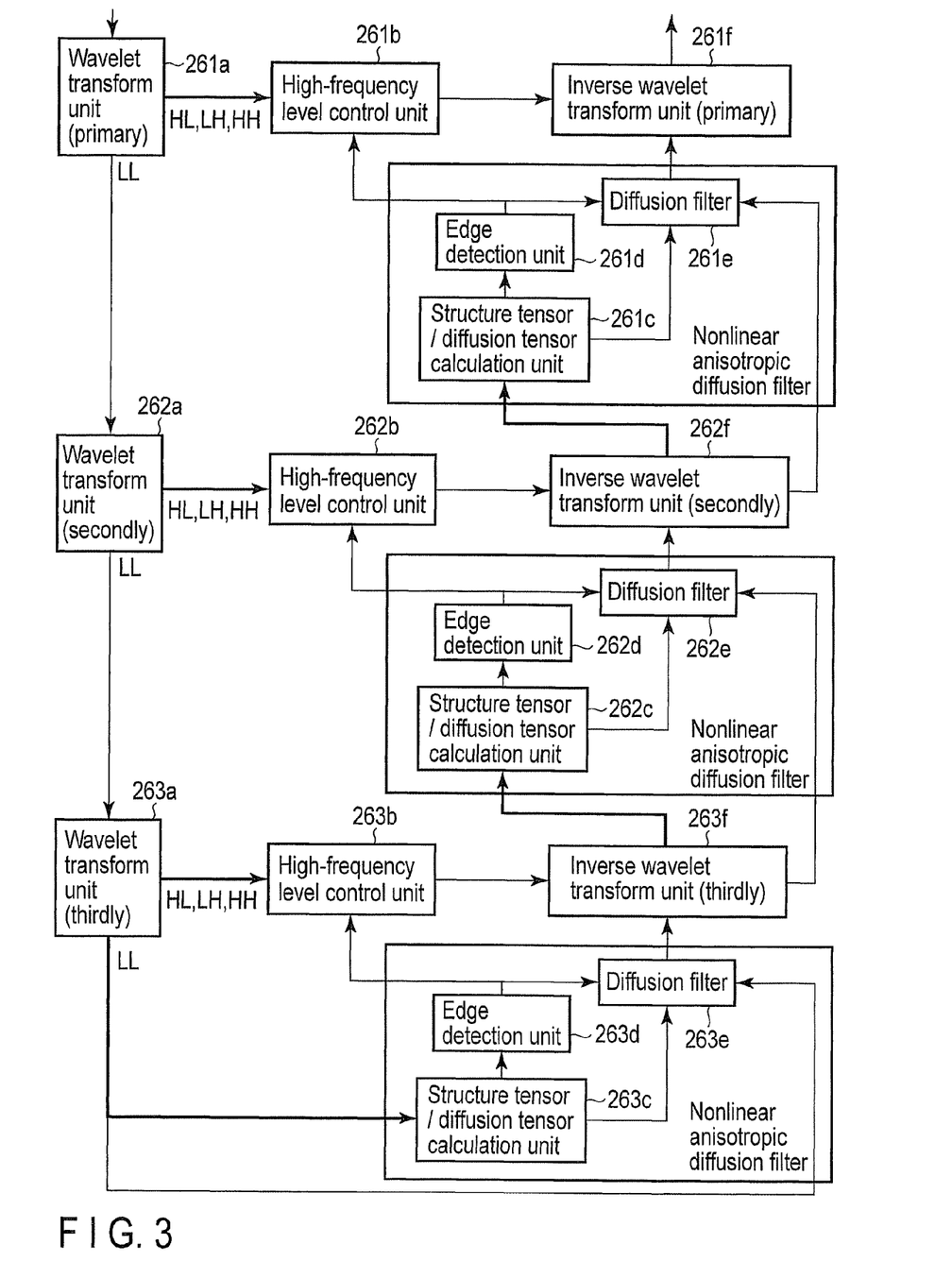
FIG. 3 is a diagram illustrating a flow of speckle reduction processing executed by a conventional speckle reduction processing unit 26.

FIG. 3 is a diagram for explaining a speckle reduction function of a conventional ultrasonic diagnostic apparatus. As shown in FIG. 3, in the conventional example, a low-frequency image (LL) decomposed with multi-resolution or an image obtained by applying nonlinear diffusion processing to a multi-resolution analysis image of a lower level is used as an input to a nonlinear anisotropic diffusion processing. Therefore, edges tend to be detected in edge detection processing performed in the nonlinear anisotropic diffusion processing in such a manner that macro-scale edges are emphasized, which does not necessarily match edges that are sensually perceived in an original image. Therefore, the resulting image may appear to be awkward. Moreover; since a higher level edge detection processing is affected by a lower level processing, it is difficult to effectively apply speckle reduction at lower levels.

In contrast, in the ultrasonic diagnostic apparatus according to the present embodiment, high-frequency decomposed image data obtained from multi-resolution analysis are used as an input to edge detection algorithm, and in the diffusion processing executed after the edge detection, the edge information detected by the high-frequency decomposed image data and the low-frequency decomposed image data are used to perform speckle reduction with the synergistic effect of the multi-resolution decomposition and the nonlinear anisotropic diffusion filter processing. Therefore, the image subjected to the edge detection processing appears more likely to be original image, and this enables the edge detection and the edge emphasis more consistent with the feeling. At the same time, since the nonlinear anisotropic diffusion processing in a lower level and the edge detection processing in a higher level are separated, the speckle reduction in the lower level can be applied more effectively.

Figure 4:
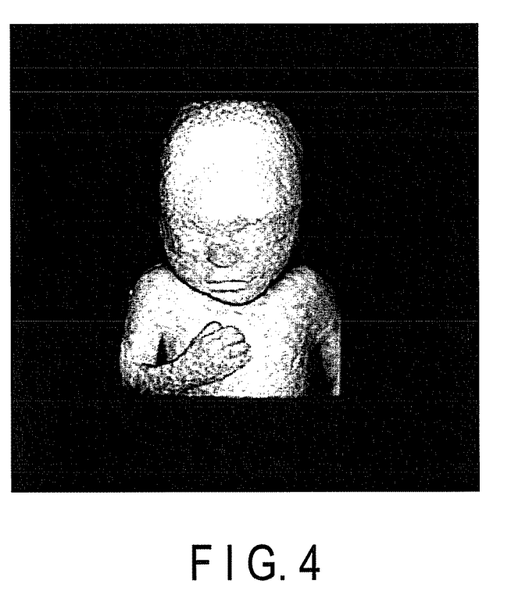
FIG. 4 is an example of an input image used in a speckle reduction function.
Figure 5:
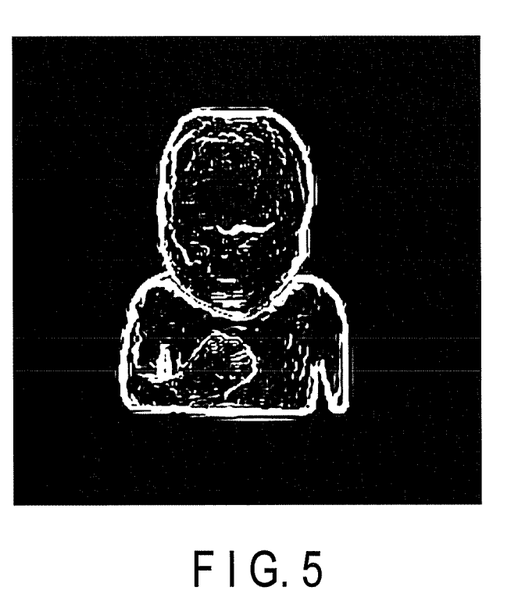
FIG. 5 is a diagram illustrating edge information received from the conventional speckle reduction function as shown in FIG. 3 using the image as shown in FIG. 4 as an input.
Figure 6:
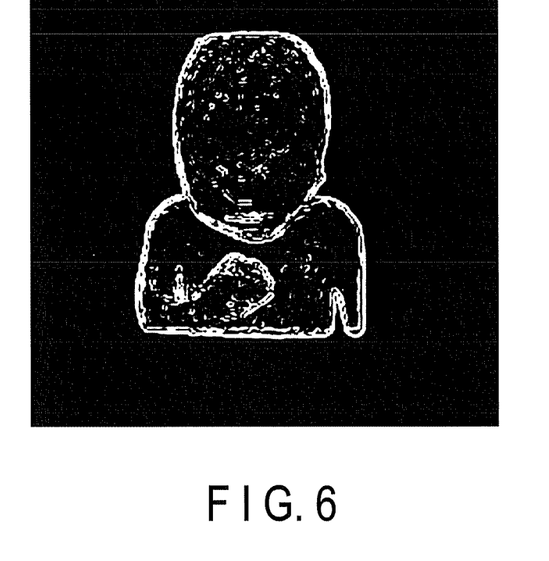
FIG. 6 is a diagram illustrating edge information received from the speckle reduction function according to the present embodiment as shown in FIG. 2 using the image as shown in FIG. 4 as an input.
Figure 7:
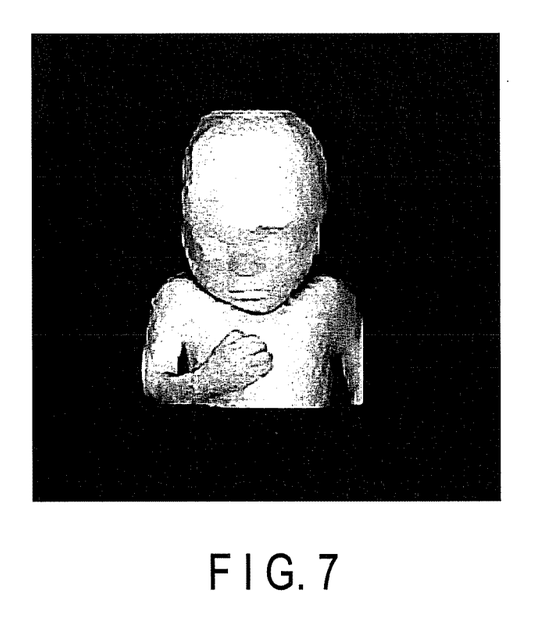
FIG. 7 is a diagram illustrating an image ultimately output by the conventional speckle reduction function as shown in FIG. 3 using the image as shown in FIG. 4 as an input.
Figure 8:
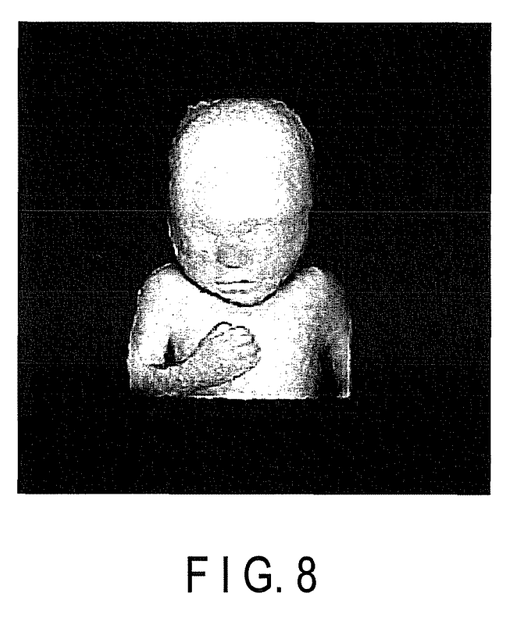
FIG. 8 is a diagram illustrating an image ultimately output by the speckle reduction function according to the present embodiment as shown in FIG. 2 using the image as shown in FIG. 4 as an input.

FIG. 4 is an example of an input image used in the speckle reduction function. FIG. 5 is a diagram illustrating edge information received from the conventional speckle reduction function as shown in FIG. 3 using the image as shown in FIG. 4 as an input. FIG. 6 is a diagram illustrating edge information received from the speckle reduction function according to the present embodiment as shown in FIG. 2 using the image as shown in FIG. 4 as an input. FIG. 7 is a diagram illustrating an image ultimately output by the conventional speckle reduction function as shown in FIG. 3 using the image as shown in FIG. 4 as an input. FIG. 8 is a diagram illustrating an image ultimately output by the speckle reduction function according to the present embodiment as shown in FIG. 2 using the image as shown in FIG. 4 as an input.

As can be understood from comparison between FIGS. 5 and 6, edges in the facial portion in the edge information obtained by the speckle reduction function according to the present embodiment are emphasized more naturally than the conventional example. As can be understood from comparison between FIGS. 7 and 8, the present embodiment enables the edge detection and the edge emphasis more consistent with the feeling than the conventional example, and can suppress unnatural edge emphasis at a relatively large structure portion appearing on a facial surface of an embryo and the like. In the nonlinear anisotropic diffusion processing in a lower level, detailed edge information is not suppressed, and accordingly, the speckle reduction in the lower level can be applied more effectively. Therefore, an edge in a relatively small structure portion such as fingers of an embryo can be appropriately emphasized, and speckle reduction processing can be realized with finer speckle and clearer interface of tissues. As a result, high quality diagnostic image can be provided, and the present embodiment contributes to the improvement of the quality of image diagnosis.

Second Embodiment

In the first embodiment, speckle reduction processing is executed on two-dimensional image data (raw data), for example. In contrast, for example, the ultrasonic diagnostic apparatus according to the present embodiment 1 executes the speckle reduction processing on three-dimensional volume data (raw data).

Figure 9:
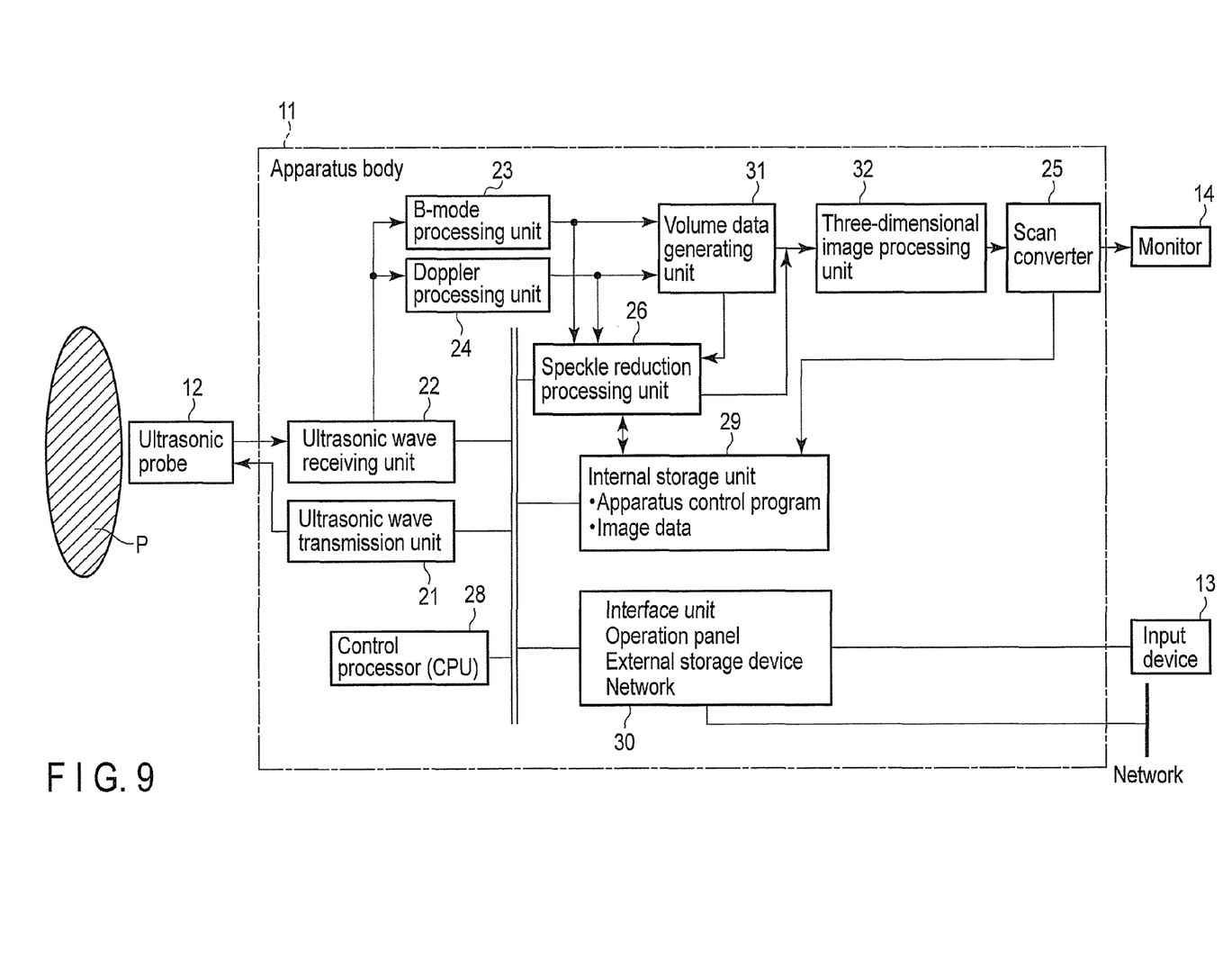
FIG. 9 is a diagram illustrating a configuration of an ultrasonic diagnostic apparatus 1 according to the second embodiment.

FIG. 9 is a diagram illustrating a configuration of an ultrasonic diagnostic apparatus 1 according to the present embodiment. The present embodiment is different from FIG. 1 in that a volume data generating unit 31 is additionally provided, and a speckle reduction processing unit 26 performs speckle processing on volume data received from a volume data generating unit 31.

The volume data generating unit 31 generates B-mode volume data using B-mode image data received from a B-mode processing unit 23. Further, the volume data generating unit 31 generates Doppler mode image volume data using Doppler mode data received from a Doppler processing unit 24.

A three-dimensional image processing unit 32 performs predetermined image processing, such as volume rendering, multi planar reconstruction (MPR), and maximum intensity projection (MIP), on the volume data received from the volume data generating unit 31 or the B-mode volume data which is received from the speckle reduction processing unit 26 and has been subjected to speckle reduction processing.

Figure 10A:
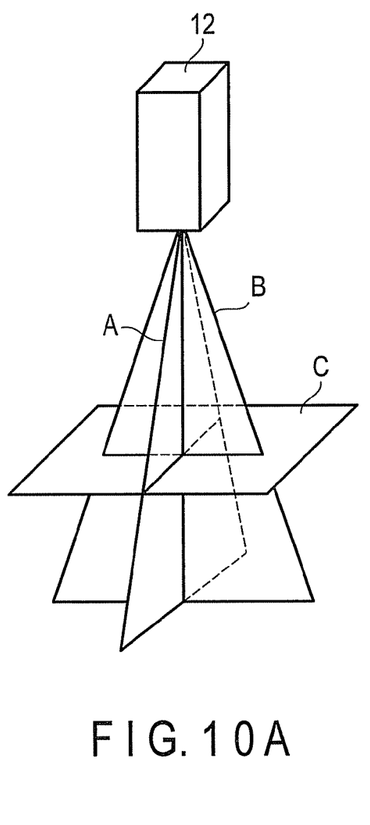
FIGS. 10A, 10B are diagrams for explaining a speckle removing function according to the second embodiment.
Figure 10B:
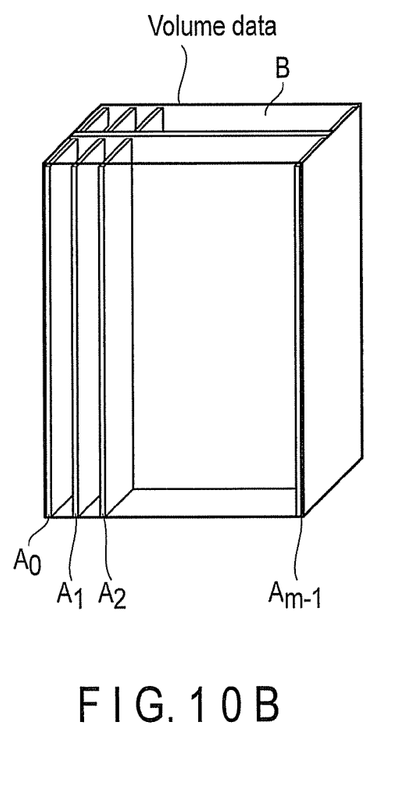

FIGS. 10A, 10B are diagrams for explaining a speckle removing function according to the present embodiment. As shown in FIGS. 10A and 10B, among cross sections volume data, two faces which cross a central axis of an object region (ultrasonic scan region) of ultrasonic scan executed by using the ultrasonic probe 12 and which are perpendicular to each other are defined as A face and B face, and a face perpendicular to the central axis and the A and B faces is defined as a C face.

The B-mode volume data received from the volume data generating unit 31 may be assumed to be a group (i.e., a group of two-dimensional image data parallel to the A face) of "m" planes $A_0, A_1, \ldots A_{m-1}$ parallel to the A face. The speckle reduction processing unit 26 executes speckle reduction processing on the B-mode volume data by performing the speckle reduction processing described in the first embodiment on all two-dimensional image data parallel to the A face.

The three-dimensional image processing unit 32 receives the B-mode volume data subjected to the speckle reduction processing from the speckle reduction processing unit 26 and the Doppler volume data from the volume data generating unit 31 and executes image processing, such as volume rendering, on the basis of the B-mode volume data and the Doppler volume data. Three-dimensional image data generated by the image processing is converted into a scanning line signal sequence in a generally-available video format by a scan converter 25 and is displayed on a monitor 14 in a predetermined form.

In the ultrasonic diagnostic apparatus according to the present embodiment, the speckle reduction processing as shown in the first embodiment can be executed on the entire B-mode volume data by performing the speckle reduction processing on all of the two-dimensional image data that forms the B-mode volume data. As a result, an ultrasonic image from which speckle is reduced can be acquired not only on the A face but about the B and C faces. Particularly on the C face which is required to be smooth, the speckle is fine and an interface of tissues becomes clearer. Accordingly, effective speckle removal can be realized in the entire three-dimensional space.

Third Embodiment

In the second embodiment, for example, the speckle reduction processing according to the first embodiment is executed on the B-mode volume data prior to three-dimensional image processing. In contrast, in the following explanation, the ultrasonic diagnostic apparatus 1 according to the present embodiment executes the speckle reduction processing on the image data having been subjected to the three-dimensional image processing.

Figure 11:
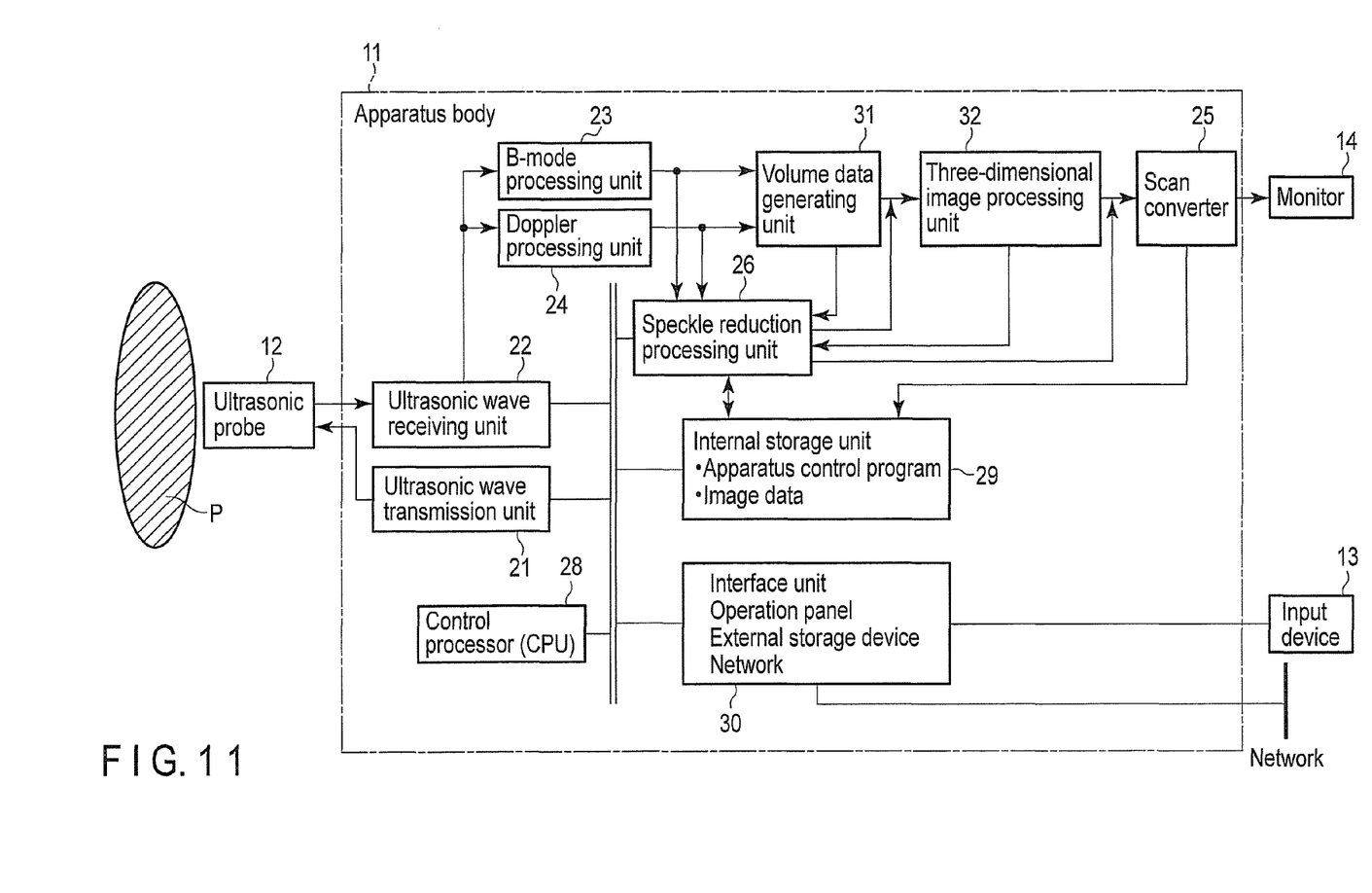
FIG. 11 is a diagram illustrating a configuration of an ultrasonic diagnostic apparatus 1 according to the third embodiment.

FIG. 11 is a diagram illustrating a configuration of an ultrasonic diagnostic apparatus 1 according to the present embodiment. The present embodiment is different from FIG. 9 in that a speckle reduction processing unit 26 performs speckle processing on image data received from a three-dimensional image processing unit 32.

Figure 12:
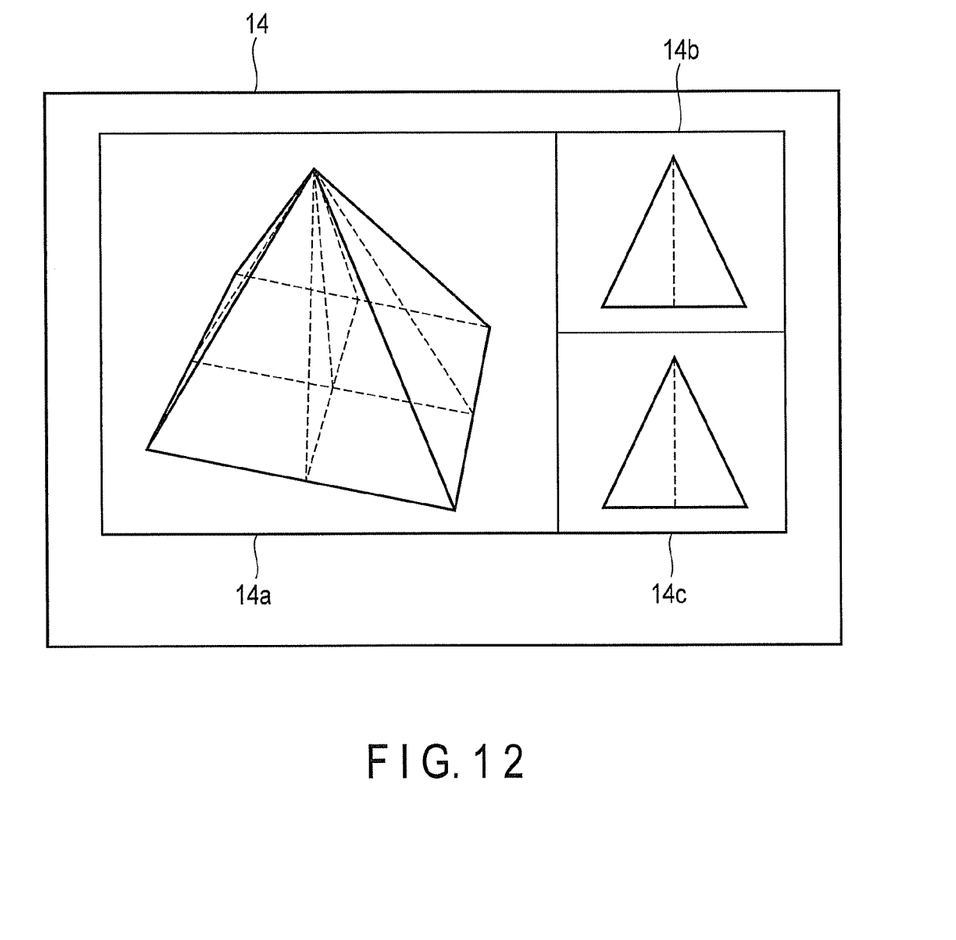
FIG. 12 is a diagram illustrating an example of a mode in which a plurality of three-dimensional images (a volume rendering image 14a, a first multi planar reconstruction image 14b, and a second multi planar reconstruction image 14c) are displayed simultaneously on a monitor 14.

FIG. 12 is a diagram illustrating an example of a mode in which a plurality of three-dimensional images (a volume rendering image 14a, a first multi planar reconstruction image 14b, and a second multi planar reconstruction image 14c) are displayed simultaneously on a monitor 14.

The speckle reduction processing unit 26 executes, for example, the speckle reduction processing, which was described in the first embodiment, on three-dimensional image data received from the three-dimensional image processing unit 32. In this case, for example, when a display form shown in FIG. 12 is adopted, the speckle reduction processing may be performed on at least one of the volume rendering image 14a, the first multi planar reconstruction image 14b, and the second multi planar reconstruction image 14c. In addition, it is to be understood that the three-dimensional image data received from the three-dimensional image processing unit 32 is not limited to examples of the volume rendering image 14a, the first multi planar reconstruction image 14b, and the second multi planar reconstruction image 14c. For example, the speckle reduction processing may also be executed on three-dimensional image data obtained by other rendering and reconstruction processing, such as surface rendering and maximum intensity projection.

Fourth Embodiment

In an ultrasonic diagnostic apparatus according to the fourth embodiment, the speckle reduction function according to a different flow of signal will be explained. More specifically, in the configuration of the first to third embodiments, the output data from a lower level, the edge information from the edge detection unit, and the high-frequency image received from the high-frequency level control unit are used as a input to generate the high-frequency image and the low-frequency image on which the edge emphasis and the speckle reduction are executed, and the high-frequency image and the low-frequency image are transformed by inverse wavelet transformation and output to a higher level. In contrast, in the configuration of the ultrasonic diagnostic apparatus according to the fourth embodiment, in each layer other than the lowermost layer, the low-frequency image (LL) obtained from the wavelet conversion in each layer, edge information received from the edge detection unit, and each element of the structure tensor calculated by the structure tensor/diffusion tensor calculation unit 263c are received as an input to generate the low-frequency image on which the edge emphasis and the speckle reduction are executed and are output to a lower level.

Figure 13:
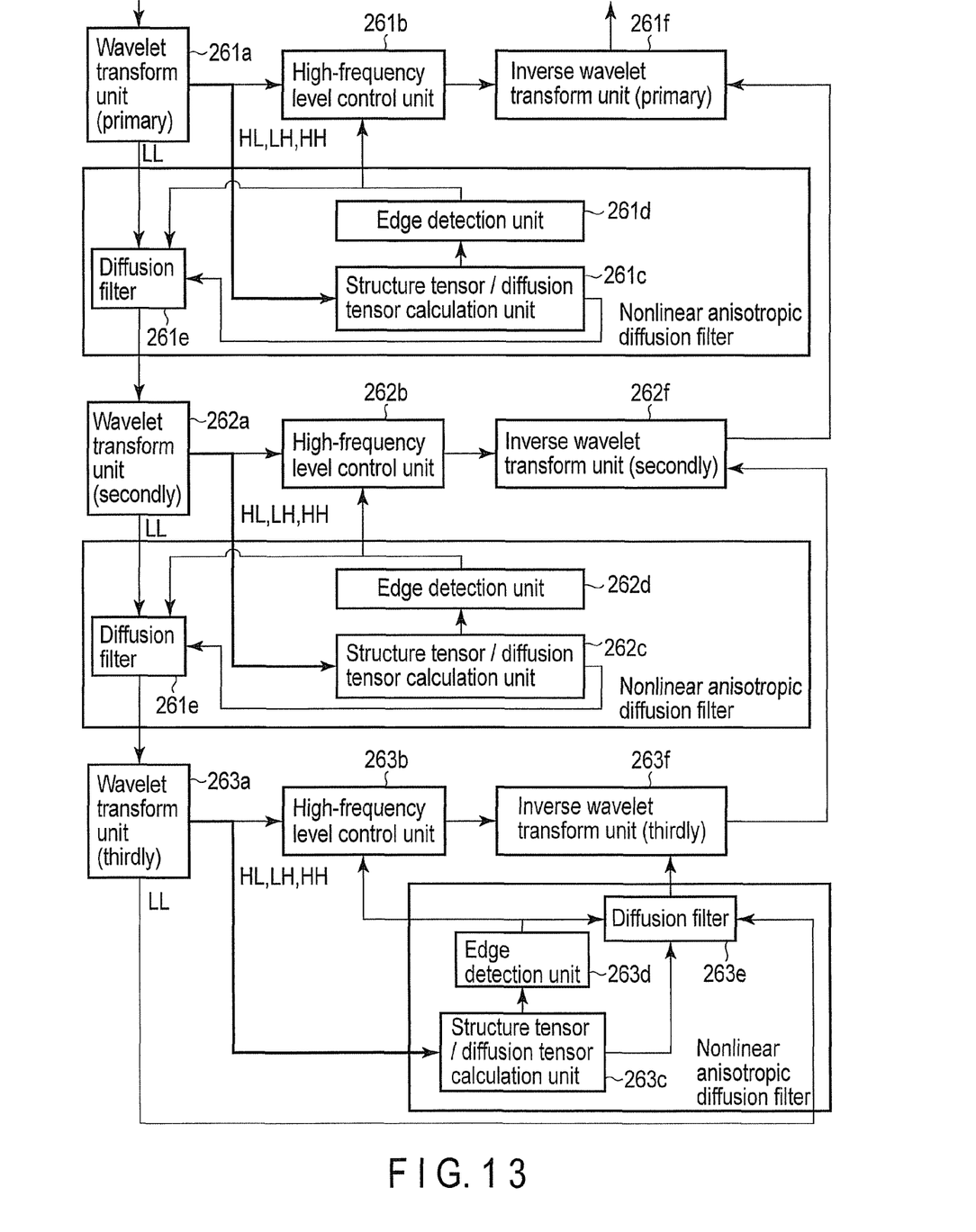
FIG. 13 is a diagram illustrating the flow of the speckle reduction processing.

It should be noted that which of the speckle reduction function according to the first to third embodiments or the speckle reduction function according to the fourth embodiment is employed is selected on the basis of a target of diagnosis, for example. In the explanation below, for example, the speckle reduction processing is executed on the two-dimensional image data (raw data), for example. However, as explained in the second and third embodiments, it may be possible to use three-dimensional image data (raw data) or image data having been subjected to the image processing using and the raw data. FIG. 13 is a diagram illustrating the flow of the speckle reduction processing according to the present embodiment. As shown in the drawing, first, a wavelet transform unit 261a of level 1 performs multi-resolution decomposition of image data (raw data) input from a B-mode processing unit 23. As a result of the multi-resolution decomposition, image data after decomposition is decomposed into a low-frequency image (LL), a horizontal direction high-frequency image (LH), a vertical direction high-frequency image (HL), and a diagonal direction high-frequency image (HH), of which horizontal and vertical lengths are half of those before the decomposition. Among the decomposed image data, the low-frequency image (LL) is output to a diffusion filter 261e, and the horizontal direction high-frequency image (LH), the vertical direction high-frequency image (HL), and the diagonal direction high-frequency image (HH) are respectively output to a high-frequency level control portion 261b and a structure tensor/diffusion tensor calculation unit 261c of level 1.

Subsequently, a structure tensor/diffusion tensor calculation unit 261c of level 1 calculates a structure tensor and a diffusion tensor using the horizontal direction high-frequency image (LH), the vertical direction high-frequency image (HL), and the diagonal direction high-frequency image (HH). An edge detection unit 2631 calculates the sizes of edges (edge information) from each element of the structure tensor calculated by the structure tensor/diffusion tensor calculation unit 261c. The calculated edge information is output to the diffusion filter 261e. The high-frequency level control unit 261b of level 1 receives the horizontal direction high-frequency image (LH), the vertical direction high-frequency image (HL), the diagonal direction high-frequency image (HH), and edge information on these three components, and controls a high-frequency level according to the images and the edge information.

Subsequently, the diffusion filter 261e of level 1 filters the low-frequency image (LL) input from the wavelet transform unit 261a using each element of the structure tensor calculated by the structure tensor/diffusion tensor calculation unit 263c and the edge information received from the edge detection unit 261d and outputs the low-frequency image, on which the edge emphasis and the speckle reduction in level 1 are executed, to the wavelet transform unit 262a of level 2.

In level 2, the same processing as level 1 is executed using the low-frequency image output from level 1. In level 3, the same processing as the processing of level 3 explained in the first embodiment is executed using the low-frequency image output from level 2.

The inverse wavelet transform unit 263f of level 3 restructures one image using the low-frequency image data received from the diffusion filter 263e and the high-frequency image data received from the high-frequency level control unit 263b. The horizontal and vertical lengths of the restructured image are twice those of an input image.

The restructured image output from the inverse wavelet transform unit 263f of level 3 is output to the inverse wavelet transform unit 262f of level 2. The inverse wavelet transform unit 262f restructures one image using the restructured image received from the inverse wavelet transform unit 263f and the high-frequency image data received from the high-frequency level control unit 262b. Further, the inverse wavelet transform unit 261f restructures one image using the restructured image received from the inverse wavelet transform unit 262f and the high-frequency image data received from the high-frequency level control unit 261b. As a result of these processings, image data having been efficiently subjected to the edge emphasis and the speckle reduction are ultimately generated in the inverse wavelet transform unit 261f, and the image data are output to the scan converter 25.

The scan converter 25 mixes the composite image data with character information, scale, and the like of various parameters, converts the result into a scanning line signal sequence in a generally-available video format such as a television, and generates an ultrasonic diagnostic image as a display image. The generated ultrasonic image is displayed on the monitor 14 in a predetermined form.

According to the above configuration, the speckle reduction can be applied effectively. As a result, an edge in a relatively small structure portion can be appropriately emphasized, and speckle reduction processing can be realized with finer speckle and clearer interface of tissues.

The present embodiments are not limited to the embodiments described above but may be embodied upon modifying constituent components without departing from the gist of each present embodiment when the present embodiments are carried out. For example, specific modifications include the following examples.

(1) Each of the functions in the present embodiment may be realized by installing a program, which is used to execute corresponding processing, in a computer, such as a workstation, and then loading the program onto a memory. At this occasion, a program capable of causing a computer to execute a corresponding technique may be distributed in such a manner that the program is stored in a recording medium, such as a magnetic disk (for example, a floppy (registered trademark) disk or a hard disk), an optical disk (for example, a CD-ROM or a DVD), and a semiconductor memory.

(2) In the second embodiment described above, a surface crossing the central axis of an ultrasonic scan region is set as a cross section on which the speckle reduction processing is performed. However, the speckle reduction processing may be performed on any given cross section of a three-dimensional space without being limited to the example.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising circuitry configured to perform:
   executing transmission and reception of an ultrasonic wave in a B-mode with respect to a predetermined region of a tested body to generate ultrasonic image data;
   hierarchically performing multi-resolution decomposition of the ultrasonic image data to acquire low-frequency decomposed image data with first to n-th levels and high-frequency decomposed image data with first to n-th levels, where "n" is a natural number equal to or larger than 2;
   calculating a filter coefficient using the high-frequency decomposed image data in each layer obtained by performing the multi-resolution decomposition;
   using the filter coefficient to perform nonlinear anisotropic diffusion filtering on the low-frequency decomposed image data or obtained data from a next lower layer and generate edge information on a signal, for every layer, from the high-frequency decomposed image data,
   controlling a signal level of the high-frequency decomposed image data in each layer obtained by performing the multi-resolution decomposition for every layer on the basis of the edge information of each of the layers; and
   acquiring ultrasonic image data by hierarchically performing multi-resolution mixing of data obtained by the nonlinear anisotropic diffusion filtering or data from a next lower layer and data obtained by the controlling.

2. The ultrasonic diagnostic apparatus according to claim 1, wherein the multi-resolution decomposition is wavelet transform, and the multi-resolution mixing is inverse wavelet transform.

3. The ultrasonic diagnostic apparatus according to claim 1, wherein each of the multi-resolution decomposition and the multi-resolution mixing is a Laplacian pyramid method.

4. The ultrasonic diagnostic apparatus according to claim 1, wherein the ultrasonic image data are raw data prior to scan conversion processing.

5. The ultrasonic diagnostic apparatus according to claim 1, wherein the ultrasonic image data are volume data, and the processing circuitry executes the multi-resolution decomposition on each of a plurality of two-dimensional ultrasonic image data that forms the volume data.

6. The ultrasonic diagnostic apparatus according to claim 1, wherein the ultrasonic image data are volume data, and the processing circuitry executes the multi-resolution decomposition on three-dimensional image data generated by using the volume data.

7. An ultrasonic image processing apparatus comprising circuitry configured to perform:
   hierarchically performing multi-resolution decomposition of ultrasonic image data obtained by performing transmission and reception of an ultrasonic wave in a B-mode with respect to a predetermined region of a tested body to acquire low-frequency decomposed image data with first to n-th levels and high-frequency decomposed image data with first to n-th levels, where "n" is a natural number equal to or larger than 2;
   calculating a filter coefficient using the high-frequency decomposed image data in each layer obtained by performing the multi-resolution decomposition;
   using the filter coefficient to perform nonlinear anisotropic diffusion filtering on the low-frequency decomposed image data or obtained data from a next lower layer and generate edge information on a signal, for every layer, from the high-frequency decomposed image data,
   controlling a signal level of the high-frequency decomposed image data in each layer obtained by performing the multi-resolution decomposition for every layer on the basis of the edge information of each of the layers; and
   acquiring ultrasonic image data by hierarchically performing multi-resolution mixing of data obtained by the nonlinear anisotropic diffusion filtering or data from a next lower layer and data obtained by the controlling.

8. The ultrasonic image processing apparatus according to claim 7, wherein the multi-resolution decomposition is wavelet transform, and the multi-resolution mixing is inverse wavelet transform.

9. The ultrasonic image processing apparatus according to claim 7, wherein each of the multi-resolution decomposition and the multi-resolution mixing is a Laplacian pyramid method.

10. The ultrasonic image processing apparatus according to claim 7, wherein the ultrasonic image data are raw data prior to scan conversion processing.

11. The ultrasonic image processing apparatus according to claim 7, wherein the ultrasonic image data are volume data, and the processing circuitry executes the multi-resolution decomposition on each of a plurality of two-dimensional ultrasonic image data that forms the volume data.

12. The ultrasonic image processing apparatus according to claim 7, wherein the ultrasonic image data are volume data, and the processing circuitry executes the multi-resolution decomposition on three-dimensional image data generated by using the volume data.

* * * * *